United States Patent
Gulati (10) Patent No.: US 6,920,397 B2
(45) Date of Patent: *Jul. 19, 2005

(54) REPEATABLE SOFTWARE-BASED ACTIVE SIGNAL PROCESSING TECHNIQUE

(75) Inventor: Sandeep Gulati, La Canada Flintridge, CA (US)

(73) Assignee: ViaLogy Corp., Altadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/677,402

(22) Filed: Oct. 1, 2003

(65) Prior Publication Data

US 2004/0063136 A1 Apr. 1, 2004

Related U.S. Application Data

(63) Continuation of application No. 09/913,131, filed as application No. PCT/US00/04150 on Feb. 17, 2000, now Pat. No. 6,780,589.

(51) Int. Cl.[7] .................... G01N 33/48; G01N 33/53; C12Q 1/68
(52) U.S. Cl. .................. 702/19; 435/6; 435/7.1
(58) Field of Search .................... 702/19, 11; 435/6, 435/7.1, 69.1

(56) References Cited

U.S. PATENT DOCUMENTS

| 4,686,695 | A | * | 8/1987 | Macovski | .................. 378/146 |
|---|---|---|---|---|---|
| 5,236,826 | A | * | 8/1993 | Marshall | .................. 435/7.92 |
| 5,784,162 | A | | 7/1998 | Cabib et al. | |
| 6,136,541 | A | | 10/2000 | Gulati | |
| 6,142,681 | A | * | 11/2000 | Gulati | .................. 702/19 |
| 6,671,625 | B1 | * | 12/2003 | Gulati | .................. 702/20 |
| 6,780,589 | B1 | * | 8/2004 | Gulati | .................. 435/6 |

* cited by examiner

Primary Examiner—Ardin H. Marschel
(74) Attorney, Agent, or Firm—Fish & Richardson P.C.

(57) ABSTRACT

A technique is disclosed that is useful for determining the presence of specific hybridization expression within an output pattern generated from a digitized image of a biological sample applied to an arrayed platform. The output pattern includes signals associated with noise, and signals associated with the biological sample, some of which are degraded or obscured by noise. The output pattern is first segmented using tessellation. Signal processing, such as interferometry, or more specifically, resonance interferometry, and even more specifically quantum resonance interferometry or stochastic resonance interferometry, is then used to amplify signals associated with the biological sample within the segmented output pattern having an intensity lower than the intensity of signals associated with noise so that they may be clearly distinguished from background noise. The improved detection technique allows repeatable, rapid, reliable, and inexpensive measurements of arrayed platform output patterns.

20 Claims, 6 Drawing Sheets

REPEATABLE SOFTWARE-BASED ACTIVE SIGNAL PROCESSING TECHNIQUE

CLAIM OF PRIORITY

This application is continuation of U.S. Pat. No. 09/913,131, filed on Aug. 9, 2001 now U.S. Pat. No. 6,780,598, which is a national stage application of PCT US00/04150 filed on Feb. 17, 2000, which claims priority to U.S. patent application Ser. No. 09/253,792, filed on Feb. 22, 1999, now U.S. Pat. No. 6,142,681.

FIELD OF THE INVENTION

The invention generally relates to techniques for analyzing biological samples, such as DNA or RNA samples, and in particular to techniques for analyzing the output of a hybridized biochip to which the sample has been applied.

BACKGROUND OF THE INVENTION

A variety of techniques have been developed to analyze DNA, RNA samples or other biological samples to identify diseases, mutations, or other conditions present within a patient providing the sample. Such techniques may determine, for example, whether the patient has any particular disease such as cancer or AIDS, or has a genetic predisposition toward the disease.

One particularly promising technique for analyzing biological samples uses a DNA biochip (or microarray) which generates a hybridization pattern representative of the characteristics of the DNA within the sample. Briefly, a DNA microarray includes a rectangular array of single stranded DNA fragments. Each element within the array includes millions of copies of identical single stranded strips of DNA containing specific sequences of bases. A different fragment of DNA may be provided at each different element of the array. In other words, location (1,1) contains a different single stranded fragment of DNA than location (1,2) which also differs from location (1,3) etc.

A DNA sample to be analyzed is first fragmented into individual single stranded sequences with each sequence being tagged with a fluorescent molecule. The fragments are applied to the microarray where each fragment bonds only with matching DNA fragments already embedded on the microarray. Fragments which do not match any of the elements of the microarray simply do not bond at any of the sites of the microarray and are discarded. Thus, only those microarray locations containing fragments that match fragments within the DNA sample will receive the fluorescent molecules. Typically, a fluorescent light source is then applied to the microarray to generate a fluorescent image identifying which elements of the microarray bonded with fragments of the DNA sample and which did not. The image is then analyzed to determine which specific DNA fragments were contained within the original sample and to determine therefrom whether particular diseases, mutations or other conditions are present within the DNA sample.

For example, a particular element of the microarray may be provided with fragments of DNA representative of a particular type of cancer. If that element of the array fluoresces under fluorescent illumination, then the DNA of the sample contains the DNA sequence representative of that particular type of cancer. Hence, a conclusion can be drawn that the patient providing the sample either already has that particular type of cancer or is perhaps predisposed towards that cancer. As can be appreciated, by providing a wide variety of known DNA fragments on the microarray, the resulting fluorescent image can be analyzed to identify a wide range of conditions.

Figure 1:
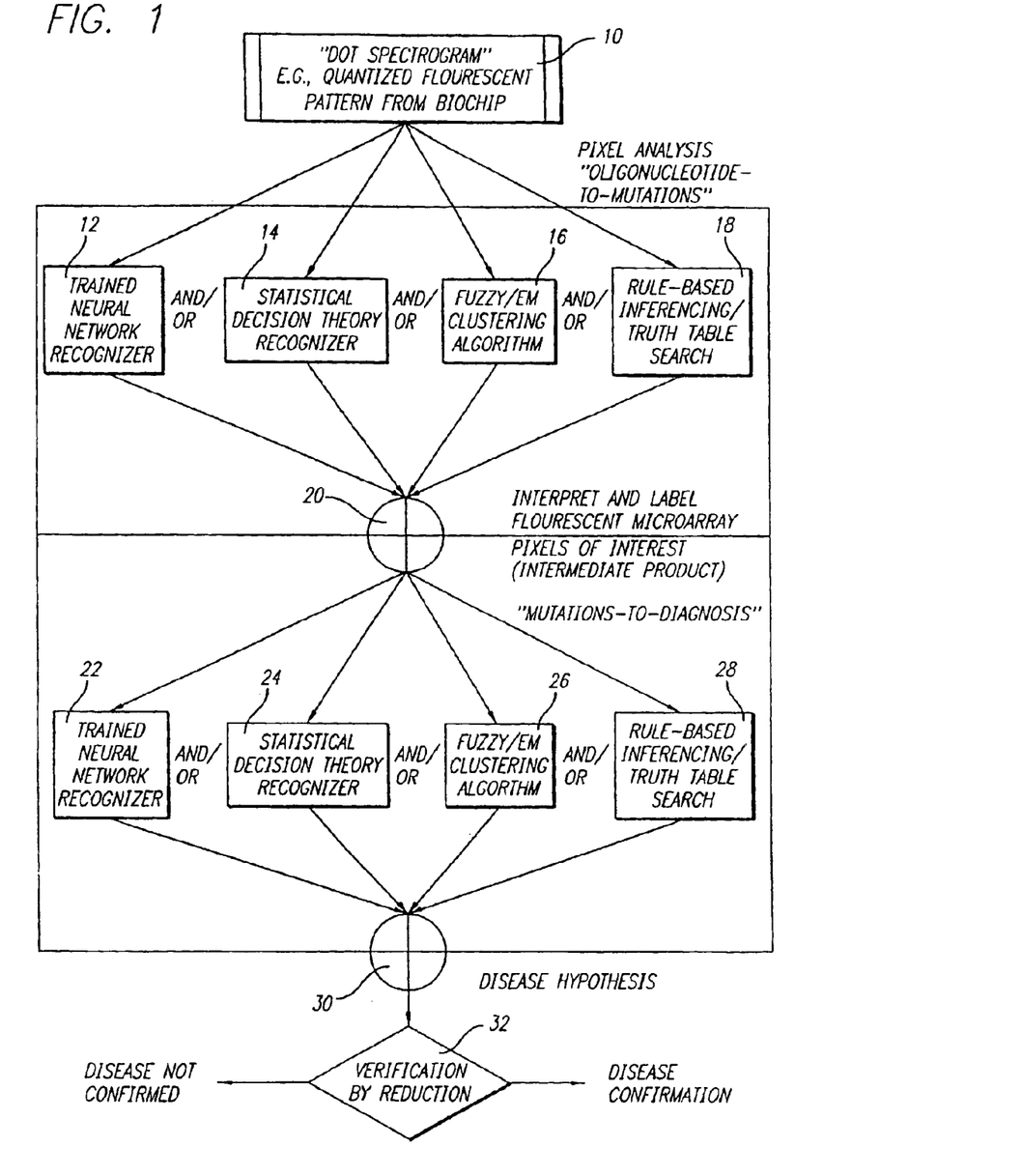
FIG. 1 is a flow chart illustrating exemplary techniques for analyzing dot spectrograms, some combinations of which are in the prior art.

Unfortunately, under conventional techniques, the step of analyzing the fluorescent pattern to determine the nature of any conditions characterized by the DNA is expensive, time consuming, and somewhat unreliable for all but a few particular conditions or diseases. FIG. 1 illustrates various conventional techniques for analyzing the fluorescent pattern. Some prior art systems utilize two or more of the techniques. It should be noted though that many combinations of the techniques are not provided in the prior art. Briefly, the fluorescent pattern is quantized to yield a dot spectrogram at step 10. Any of four different techniques are employed to identify oligonucleotides represented by the dot spectrogram and to then identify mutations based upon the oligonucleotides. More specifically, the dot spectrogram may be analyzed using a trained neural network recognizer 12, a statistical decision theory recognizer 14, a fuzzy/expectation method (EM) clustering algorithm 16 or a rule-based inferencing/truth table search 18.

The results are interpreted to yield mutations of interest at step 20. Then the mutations are again processed using either a trained neural network recognizer 22, a statistical decision theory recognizer 24, a fuzzy/EM clustering algorithm 26 or a rule-based inferencing/truth table search 28. The results are combined at step 30 to yield a diagnosis.

Finally, disease confirmation is performed at step 32 by "reduction", in other words the disease is confirmed by probabilistic inferencing.

One major problem with many conventional techniques is that the techniques have poor repeatability. Hence, if the same sample is analyzed twice, different results are often obtained. Also, the results may vary from lab to lab. Also, skilled technicians are required to operate the DNA microarrays and to analyze the output resulting in high costs. One reason that repeatability is poor is that the signatures within the dot spectrogram that are representative of mutations of interest are typically very weak and are immersed in considerable noise. Conventional techniques are not particularly effective in extracting mutation signatures from dot spectrograms in low signal to noise circumstances.

Accordingly, it would highly desirable to provide an improved method and apparatus for analyzing the output of the DNA microarray to more expediently, reliably, and inexpensively determine the presence of any conditions within the patient providing the DNA sample. It is particularly desirable to provide a technique that can identify mutation signatures within dot spectrograms even in circumstance wherein the signal to noise ration is extremely low. It is to these ends that aspects of the invention are generally drawn.

One analysis technique for achieving the aforementioned advantages is described in co-pending U.S. patent application Ser. No. 09/253,789, now U.S. Pat. No. 6,136,541, filed contemporaneously herewith, entitled "Method and Apparatus for interpreting Hybridized Biochip Patterns Using Resonant Interactions Employing Quantum Expressor Functions", (the "co-pending application") and incorporated by reference herein. Briefly, the method of the co-pending application operates as follows. The method identifies mutations, if any, present in a biological sample from a set of known mutations by analyzing a dot spectrogram representative of quantized hybridization activity of oligonucleotides in the biological sample to identify the mutations. A resonance pattern is generated which is representative of resonances between a stimulus pattern associated with the set of known mutations and the dot spectrogram. The resonance pattern is interpreted to yield a set of confirmed mutations by comparing resonances found therein with predetermined resonances expected for the selected set of mutations. In a particular example described in the co-pending application, the resonance pattern is generated by iteratively processing the dot spectrogram by performing a convergent reverberation to yield a resonance pattern representative of resonances between a predetermined set of selected Quantum Expressor Functions and the dot spectrogram until a predetermined degree of convergence is achieved between the resonances found in the resonance pattern and resonances expected for the set of mutations. The resonance pattern is then analyzed to yield a set of confirmed mutations by mapping the confirmed mutations to known diseases associated with the pre-selected set of known mutations to identify diseases, if any, indicated by the DNA sample. A diagnostic confirmation is then made by taking the identified diseases and solving in reverse for the associated Quantum Expressor Functions and then comparing those Quantum Expressor Functions with ones expected for the mutations associated with the identified disease to verify correspondence. If no correspondence is found, a new sub-set of known mutations are selected and the steps are repeated to determine whether any of the new set of mutations are present in the sample.

By exploiting a resonant interaction, mutation signatures may be identified within a dot spectrogram even in circumstances involving low signal to noise ratios or, in some cases, negative signal to noise ratios. By permitting the mutation signatures to be identified in such circumstances, the reliability of dot spectrogram analysis is thereby greatly enhanced. With an increase in reliability, costs associated with performing the analysis are decreased, in part, because there is less of a requirement for skilled technicians. Other advantages of the invention arise as well.

Although the method of the co-pending application represents a significant advance over techniques of the prior art, room for further improvement remains. In particular, it would be desirable to enhance the method of the co-pending application to achieve a higher degree of repeatability.

In particular, repeatability is affected by spatio-temporal degradation of hybridization in DNA microarrays implementing both passive and active hybridization. In bioelectronic systems implementing passive hybridization, sources affecting repeatability of analysis results include:

Stochastic variability in chemical kinetics

Immobilized oligonucleotide damage during fabrication

Uneven kinetics during thermally facilitated fluidics reaction

Post hybridization thermal degradation. Currently biochips are "amplification limited".

This is in large part due to losses during high-temperature hybridization downstream. During periods when the sample temperature changes from high to low or low to high, extraneous, undesirable reactions can occur that consume important reagents and create unwanted and interfering chemicals. Rapid transitions ensure that the sample spends a minimum of time at undesirable intermediate temperatures, so that the amplified DNA product has optimum fidelity and purity. So current methods rely on excessive amplification to compensate for these losses.

Oligonucleotide entanglement

Environmental decoherence due to energy and radiation

Uneven fluidic catalysis

Unstable fluorescence and chemiluminiscence marker binding

Spontaneous emissions

Partial bindings

Anti-aliasing during readout and digitization

Active hybridization is degraded by

Capacitive coupling between elements of the immobilized matrix

Partial bindings due to current leakage and uneven conductance

Ultrascale quantum squeeze effects

Spontaneous emission

Nonspecific oligonucleotide trapping

Chaotic relaxation across the array

Hence, aspects of the present invention are directed, in part, to providing enhanced repeatability of biological sample analysis despite these factors.

SUMMARY OF THE INVENTION

In accordance with a first aspect of the invention, a method is provided for identifying mutations, if any, present in a biological sample. The method operates to analyze a biochip output pattern generated using the sample to identify the mutations in the sample. In accordance with the method the output pattern is tessellated. A stimulus pattern associated with the set of known mutations is generated. A resonance pattern is then generated which is representative of resonances between the stimulus pattern and the tessellated output patterns. The resonance pattern is interpreted to yield a set of confirmed mutations by comparing resonances found therein with predetermined resonances expected for the selected set of mutations.

In an exemplary embodiment, the output pattern is a dot spectrogram representative of quantized hybridization activity of oligonucleotides in a DNA sample. The stimulus pattern is generated based upon Quantum Expressor Functions. The dot spectrogram is tessellated to match morphological characteristics of the Quantum Expressor Functions and local parametrics are extracted. The tessellated dot spectrogram and the stimulus pattern are transformed to a metrically transitive random field via phase shifting. The resonance pattern is generated by iteratively processing the tessellated dot spectrogram by performing a convergent reverberation to yield a resonance pattern representative of resonances between the Quantum Expressor Functions and the tessellated dot spectrogram until a predetermined degree of convergence is achieved between the resonances found in the resonance pattern and resonances expected for the set of mutations. The convergent reverberation includes the step of performing a convergent reverberant dynamics resonance analysis of the tessellated dot spectrogram using the resonance stimulus pattern to identify mutations represented by the tessellated dot spectrogram. The convergent reverberation also includes the step of performing a convergent reverberant dynamics resonance analysis of the mutations using the resonance stimulus pattern to identify diagnostic conditions represented by the mutations.

Also in the exemplary embodiment, the convergent reverberant dynamics resonance analyses are performed by determining resonance dynamics relaxation values based upon the tessellated dot spectrogram and the resonance stimulus; filtering the dynamics relaxation values using ensemble boundary and complete spatial randomness (CSR) filters to yield a second set of values; applying bulk property estimators to the dynamics relaxation values to yield a third set of values; evaluating the second and third sets of values to determine a degree of resonance convergence; and then determining from the degree of resonance convergence whether a paralysis of dynamics has occurred and, if so, repeating the aforementioned steps.

In the exemplary embodiments, by tessellating the dot spectrogram to match morphological characteristics of the Quantum Expressor Functions and by exploiting a resonant interaction employing a resonance convergence check which uses extracted tessellation parametric, mutation signatures may be identified within a dot spectrogram with a high degree of repeatability. By achieving a high degree of repeatability, the reliability of dot spectrogram analysis is thereby greatly enhanced. With an increase in reliability, costs associated with performing the analysis are decreased, in part, because there is less of a requirement for skilled technicians. Other advantages of the invention arise as well.

In accordance with a second aspect of the invention, a method is provided for preconditioning a dot spectrogram representative of quantized hybridization activity of oligonucleotides in a DNA samples. The method comprises the steps of tessellating the dot spectrogram to match characteristics of a predetermined stimulus pattern yielding a tessellated image; extracting local parametrics from the tessellated image; determining whether a degree of amplitude wandering representative of the local parametrics is within a predetermined allowable generator function limit; and if not, renormalizing the tessellated image to further match spectral properties of the stimulus pattern and repeating the steps.

In accordance with a third aspect of the invention, a method is provided for performing a convergent reverberant dynamics resonance analysis of a dot spectrogram representative of quantized hybridization activity of oligonucleotides in a DNA sample to identify mutations represented thereby. The method comprising the steps of determining resonance dynamics relaxation values based upon the preconditioned dot spectrogram and the resonance stimulus; filtering the dynamics relaxation values using ensemble boundary and CSR filters to yield a second set of values; applying bulk property estimators to the dynamics relaxation values to yield a third set of values; evaluating the second and third sets of values to determine whether a predetermined degree of resonance convergence has been achieved; and determining whether a paralysis of dynamics has occurred and, if so, repeating the steps.

Among other applications, principles of the invention are applicable to the analysis of various arrayed biomolecular, ionic, bioelectronic, biochemical, optoelectronic, radio frequency (RF) and electronic microdevices. Principles of the invention are particularly applicable to mutation expression analysis at ultra-low concentrations using ultra-high density passive and/or active hybridization DNA-based microarrays. Techniques implemented in accordance with the invention are generally independent of the physical method employed to accumulate initial amplitude information from the bio-chip array, such as fluorescence labeling, charge clustering, phase shift integration and tracer imaging. Also, principles of the invention are applicable to optical, optoelectronic, and electronic readout of hybridization amplitude patterns. Furthermore, principles of the invention are applicable to molecular expression analysis at all levels of abstraction: namely DNA expression analysis, RNA expression analysis, protein interactions and protein—DNA interactions for medical diagnosis at the molecular level.

Apparatus embodiments are also provided.

BRIEF DESCRIPTION OF THE DRAWINGS

The features, objects, and advantages of the present invention will become more apparent from the detailed description set forth below when taken in conjunction with the drawings in which like reference characters identify correspondingly throughout and wherein:

FIG. 4-A is a first portion of a flowchart illustrating an exemplary method for analyzing the output of a hybridized DNA microarray in accordance with the method of the present invention.

FIG. 4-B is a second portion of flowchart illustrating an exemplary method for analyzing the output of a hybridized DNA microarray in accordance with the method of the present invention.

FIG. 4-C is a third portion of flowchart illustrating an exemplary method for analyzing the output of a hybridized DNA microarray in accordance with the method of the present invention.

DETAILED DESCRIPTION OF EXEMPLARY EMBODIMENTS

With reference to the remaining figures, exemplary embodiments of the method of the co-pending application and of the present invention will now be described. The exemplary methods will be described primarily with respect to the analysis of mutation signatures within output patterns of DNA biochip microarrays, but principles of the invention to the analysis of a wide variety of other patterns as well.

Overview of Co-Pending Application

Briefly, the exemplary method of the co-pending application exploits, among other features: (a) a novel representation, interpretation and mathematical model for the immobilized oligonucleotide hybridization patterns, represented via a dot spectrogram; (b) a new "active" biomolecular target detection and discrimination method based on quantum resonance interferometry, and (c) a new spatial hashing function that yields accurate diagnostic assessment.

To this end the exemplary method of the co-pending application exploits a fundamentally different computational paradigm for mutation expression detection in pre-enhanced dot spectrogram realizations. The method is an innovative modification to dynamically arrayed quantum stochastic resonance (QSR) for discrete system analysis. The arraying strategy is a function of the expression pathway of interest. The method depends on the molecular diagnostic spectrum being addressed. Banks of coupled quantum resonators are algorithmically designed to significantly enhance signal-to-noise (SNR) performance and fuse multiple synthetic renormalized dot spectrogram realizations to better detect pre-specified biomolecular expression patterns.

Moreover, the exemplary method of the co-pending application exploits an enhancement in previous extensions to classical stochastic resonance (SR) and array enhanced SR (AESR) in signal processing and sensor data analysis. Stochastic resonance is a phenomenon wherein the response to a sensor, modeled in terms of a bistable nonlinear dynamical system, is enhanced by applying a random noise element and a periodic sinusoidal forcing function. SR occurs when the SNR passes through a maximum as the noise level is increased.

Thus as important aspect of the exemplary method of the co-pending application involves the coupling of transformed and preconditioned discrete microarray outputs to a mathematical model for a quantum-mechanical dynamical system with specific properties. When driven in a particular manner, the coupled system exhibits a nonlinear response that corresponds to detection of phenomena of interest. The method exploits modulation of observables from a "base" (canonical continuous dynamical system), so that a selected set of spectral properties match a similar selected spectral properties of a discrete spatial tessellation substructure from an amplitude spectrogram derived from bioelectronic observables. The method further exploits the concept of convolving a discrete spatial system (derived from base mutants of interest) with a continuous asymmetric temporal system to derive a spatiotemporal input to further convolve with another discrete spatial projection (of an inherently partially stabilized spatiotemporal system).

Hence key components of the exemplary biomolecular detection method of the co-pending application are: (i) selection of a basis system; (ii) generation of designer Quantum Expressor Function (QEF) for coupling with the substrate to be analyzed; (iii) generation of a Hamiltonian to describe relaxation dynamics of the coupled system; (iv) modulation of resonance parameters to enforce early resonance; (v) and exploitation of resonance suppressors to verify detection.

Figure 2:
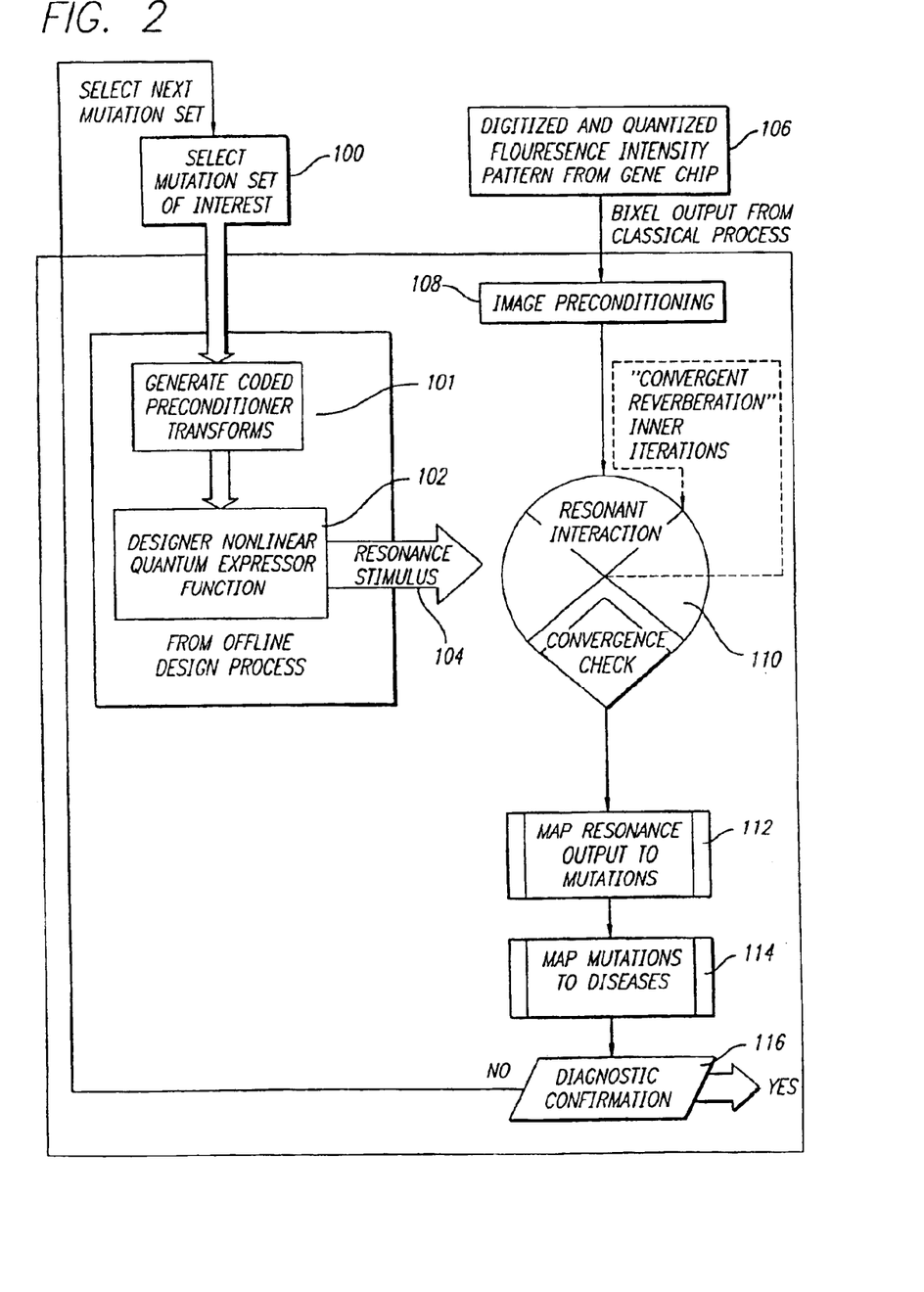
FIG. 2 is a flow chart illustrating an exemplary method for analyzing the output of a hybridized DNA microarray biochip in accordance with the method of the co-pending application.
Figure 3:
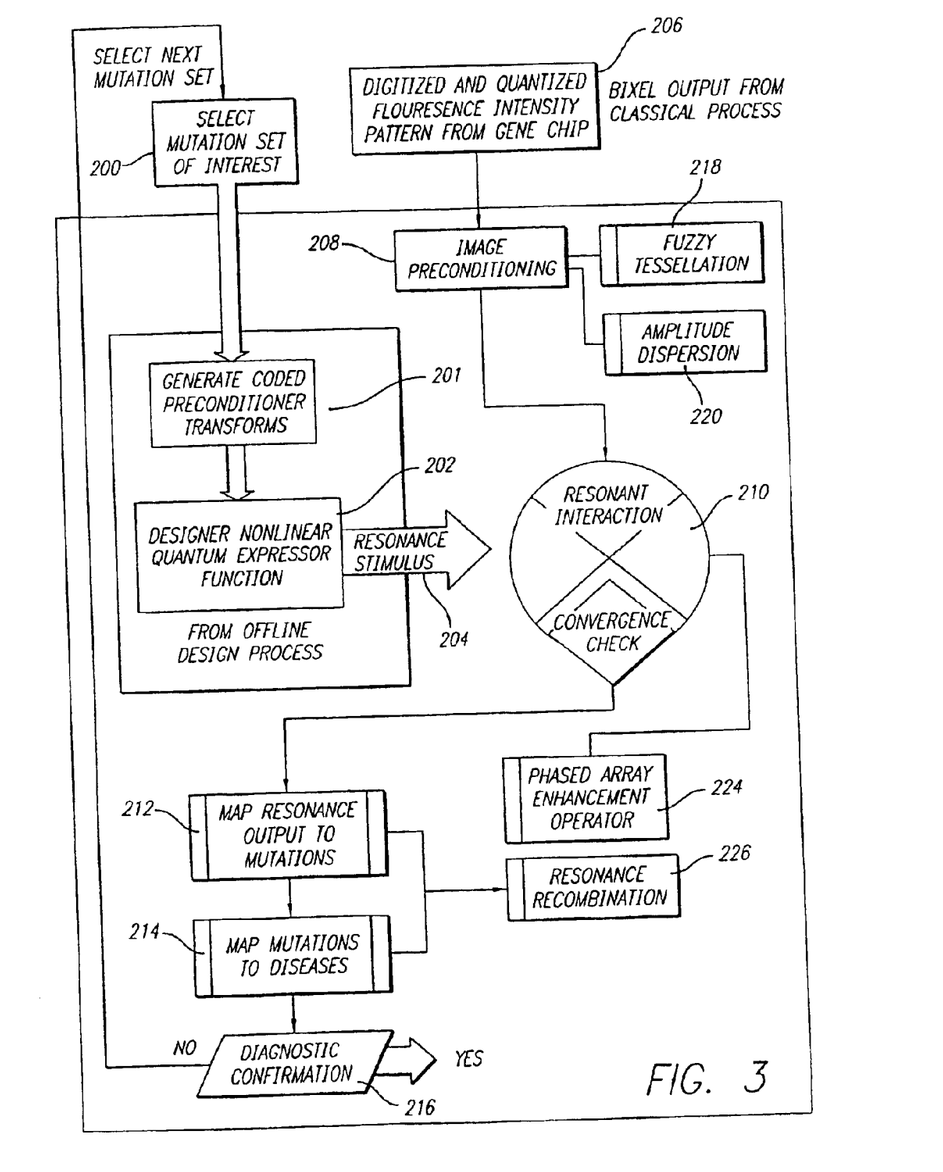
FIG. 3 is a flow chart illustrating exemplary enhancements to the method of the co-pending application provided in accordance with the present invention.

Referring to FIG. 2, initially at step 100, a set of mutations of interest are selected. The mutations, for example, may be mutations relevant to cancer, AIDS, or other diseases or conditions. At step 101, preconditioner transforms are generated based upon the selected set of mutations. The preconditioner transforms are provided to convert mutation nucleotide sequences into expected amplitude patterns in the prespecified microarray representation, given a particular biochip layout. At step 102, Quantum Expressor Functions are generated based upon the Hamiltonian of a pre-selected basis system. The Quantum Expressor Functions are designed to couple the Hamiltonian for the selected basis system to a predetermined DNA microarray configuration to permit a resonance interaction involving the output of the DNA microarray. Resonance stimulus is generated, at step 106, using the Quantum Expressor functions.

What has been summarized thus far are preliminary steps performed off-line for setting up the Quantum Expressor Functions and the corresponding resonance stimulus. These steps need be performed only once for a given set of mutations and for a given DNA microarray configuration. Thereafter, any number of output patterns from the DNA microarray may be processed using the Quantum Expressor Functions to identify whether any of the mutations of the pre-selected set of mutations are found therein. Preferably, Quantum Expressor Functions are pre-generated for a large set of mutations and for a large set of DNA microarray patterns such that, for each new DNA microarray output pattern from each new patient sample, the presence of any of the mutations can be quickly identified using the predetermined set of Quantum Expressor Functions. In general, the aforementioned steps need be repeated only to update the Quantum Expressor Functions to accommodate new and different DNA microarray patterns or to if new mutations of interest need to be considered.

At step 106, an output pattern (referred to herein as a Dot Spectrogram) is generated using a DNA microarray for which Quantum Expressor Functions have already been generated. At step 108, the dot spectrogram is preconditioned to yield a dot spectrogram tesselation (DST) to permit exploitation of a resonance between the dot spectrogram and the Quantum Expressor Functions. The actual resonant interaction, which involves convergent reverberations, is performed at step 110 until a pre-determined degree of convergence is achieved. Once convergence is achieved, a resulting resonance pattern is processed at step 112 to identify any mutations represented thereby. As will be described below, step 112 is rendered trivial by virtue of the aforementioned resonant interaction which is based upon Quantum Expressor Function already correlated with the pre-selected mutations. Hence, no complicated analysis is required to interpret the resonance pattern to identify the mutations. Next, at step 114, the mutations are mapped to corresponding diseases and conditions to thereby identify any diseases or conditions that the patient providing the sample being analyzed is afflicted with. Again, this is a fairly trivial step. Finally, at step 116, diagnostic confirmation is preformed to verify that the diseases or conditions are present in the sample. This is achieved by starting with the found diseases or conditions and then performing the steps of the method in reverse.

Each of the aforementioned steps are described in detail in the co-pending application and the detailed description thereof is not repeated herein.

Overview of the Exemplary Method of the Present Invention

The present invention is directed, in part, to improving the repeatability of the method of the co-pending application by tessellating the dot spectrogram so as to match morphological characteristics of the Quantum Expressor Functions and by using extracted local parametrics as part of a resonance convergence check during the resonance interaction. These additional steps have the advantage of establishing uncertainty bounds which permit method repeatability to be enhanced and quantified.

FIG. 3 illustrates enhancements to the technique of FIG. 2 provided by the present invention along with steps of the technique of FIG. 2. The repeated steps of FIG. 2 appearing in FIG. 3 may be the same as those of FIG. 2 and will not be redescribed. Like reference numerals, incremented by one hundred, are employed to represent the repeated steps.

Briefly the enhancements of the present invention entail five major steps:

- Preconditioning the hybridized array output pattern (i.e. the dot spectrogram) by a fuzzy tessellation and coupling the preconditioned output pattern with a canonical system with aftereffect and memory properties (step 218);
- Estimation of amplitude wanderings or dispersion (step 220);
- Implementation of resonance interaction by integrating partial or subthreshold resonances using phased array enhancement operator resonance dynamics (step 224) with additional resonances synthetically induced to accommodate the possibility for the presence of single-point and two-point mutations around the mutation-centered pixels; and
- Resonance recombination (step 226).

A combination of one or more these enhancements are superimposed on the techniques described in the co-pending patent application to address specific sources of hybridization degradation, device imperfections and protocol variability in the analysis process to thereby enhance repeatability.

Figure 4:
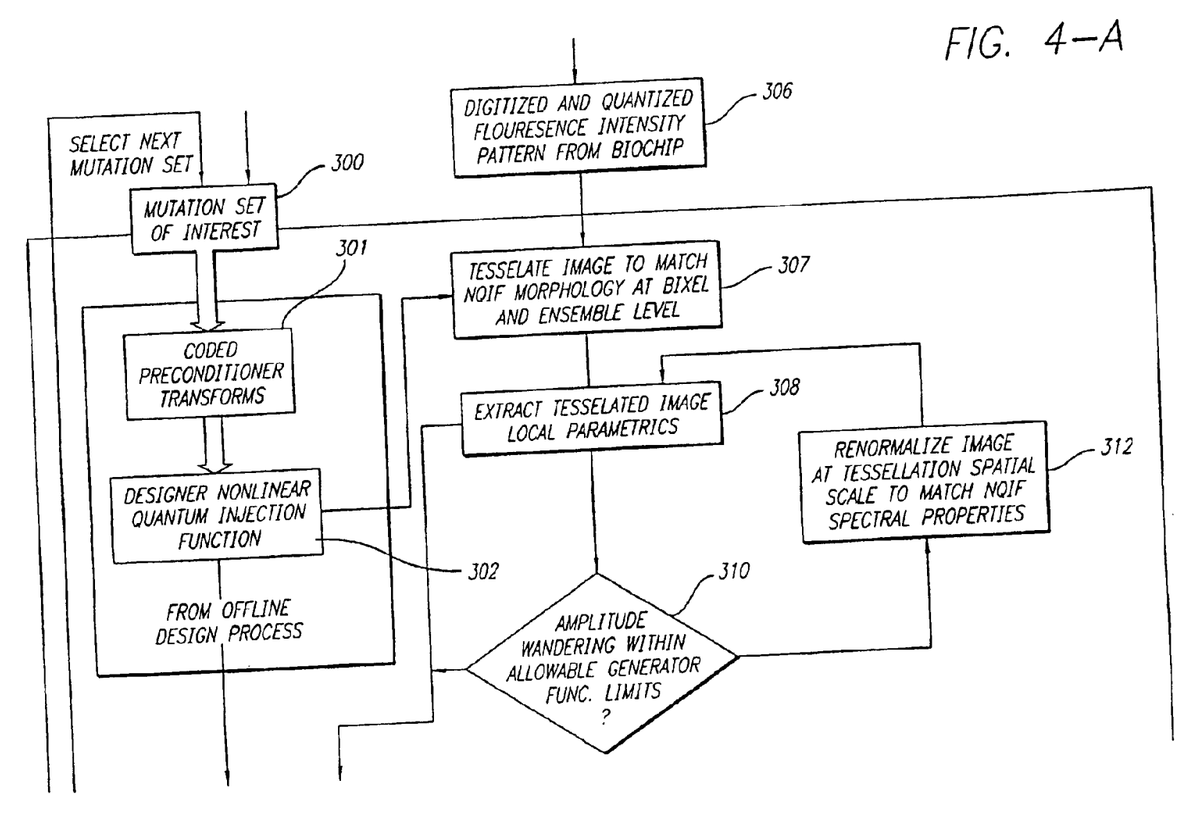

Referring now to FIGS. 4-A–4C, initially at step 300, a set of mutations of interest are selected and at step 301 preconditioner transforms are generated based upon the selected set of mutations. At step 302, Quantum Expressor Functions are generated based upon the Hamiltonian of a pre-selected basis system. Phase shifted resonance stimulus is generated, at step 304, using the Quantum Expressor functions. Grouping stimulus is also generated, at step 305.

Steps 300–305 are preferably performed off-line to set up the Quantum Expressor Functions and the corresponding resonance stimulus and grouping stimulus and need not be repeated other than to update the Quantum Expressor Functions to accommodate new and different DNA microarray patterns or if new mutations of interest need to be considered.

At step 306, a dot spectrogram is generated using a DNA microarray for which Quantum Expressor Functions have already been generated. At step 307, the dot spectrogram is tessellated to match morphological characteristics of the Quantum Expressor Functions yielding a dot spectrogram tesselation (DST). At step 308, local parametrics of the tessellated image are extracted. Then, at step 310, an amount of amplitude wandering is determined and compared with pre-determined allowable generator function limits. If, at step 310, the amplitude wandering is not within the allowable generator function limits, then execution proceeds to step 312 where the tessellated dot spectrogram to match spectral characteristics of the Quantum Expressor Functions. Steps 308 and 310 are repeated until the amplitude wandering is found to be within the pre-determined limits at which point execution proceeds to block 314 wherein a resonance interaction is performed between the tessellated, renormalized dot spectrogram and the phase shifted resonance stimulus generated at step 304 and the group stimulus generated at step 305 to identify any mutations represented by the dot spectrogram.

The actual resonant interaction, which involves convergent reverberations, includes the following sub-steps also shown in FIGS. 4A–4C. At step 316, a resonance dynamics iteration is initiated which includes the use of ensemble boundary and CSR operators (step 318) and the use of bulk property estimators (step 320). The ensemble boundary filters, CSR filters and bulk property estimators are applied to the tessellated, re-normalized dot spectrogram in combination with the resonance and group stimulus. The resulting filtered dot spectrogram is then evaluated to determine a degree of resonance convergence to one or more of the set of predetermined mutations, at step 322. The degree of convergence is evaluated, at step 324, against a Lindbald condition and, if the Lindbald condition is not met, the system is deemed to be subject to paralysis of dynamics and execution proceeds to step 326 wherein possible hixel death is compensated for by increasing a time scale for the iteration initiated at step 316 and then repeating the iteration.

Here it should be noted that mutation death and paralysis of dynamics are different concepts. The mutation death check is a conditional check. If this check shows that a resonance is not possible for a specific mutation resonance centered (MRC)-hixel then the iteration is terminated and block 314 is exited. But failure of resonance dynamics is not sufficient to conclude that a specific mutation is absent. Indeed, if the "hixel death" check fails, that implies that resonance could be still obtained in a downstream iteration.

If, at step 324, the iteration has converged and no paralysis has occurred, then one or more mutations have been reliably identified. Execution proceeds to block 325 wherein another resonant interaction is performed to identify particular diseases represented by the mutations. Briefly, at step 326, a resonance dynamics iteration is initiated which includes the use of ensemble boundary and CSR operators (step 328) and the use of bulk property estimators (step 330). The resulting filtered dot spectrogram is then evaluated to determine a degree of resonance convergence, at step 332. The degree of convergence is evaluated, at step 334, against a Lindbald condition and, if the Lindbald condition is not met, the system is deemed to be subject to paralysis of dynamics and execution proceeds to step 336 wherein a time scale for the iteration initiated at step 326 is increased before the iteration is repeated. If the Lindbald condition is met, then diseases corresponding to the mutations found using step 314 have been reliably identified.

Processing in accordance with step 335 depends on the biochip. The flowchart of FIG. 4 illustrates a general form of the method requiring processing during step 335. In other implementations, this step is trivial or can be eliminated entirely. In this regard, the overall method is implemented at two levels of abstraction, depending on how well the disease genomics is understood. Detection of a specific mutation is necessary and sufficient to conclude expression of a specific gene. But the expressed gene may not be the one to conclusively identify the disease. Then another level of abstraction is invoked wherein the method is applied inferentially by expanding the gene expression circuit or gene expression tree to determine if there is evidence that all expressed genes eventually lead to one that conclusively identifies the disease. So step 335 operates on the results of step 314, such that all identified mutations are used as an input to determine if the complete expression pathway for leading up to the point that a disease can be concluded.

If the biochip is so designed that the mutations corresponding to all intermediate expressed products, from any disease starting point can be captured by resonance output of step 314, then sub-steps within step 335 and subsequent steps 340 and 342 can be circumvented. If not, clustering step 340 and geometric hashing step 342 are provided to identify that an expression pathway is present that trivializes the disease conclusion=(step 344).

Once the diseases are identified, clustering properties are evaluated at step 340 to selectively eliminate oligonucleotides representing possible diagnoses based on morphological filtering of subthreshold resonances and any subsequent recentering (i.e., the inverse of dispersion). Steps 314–335 produce a cluster of sub-threshold resonances. Step 340 is a reverification such that all induced resonances are present in the target sample and not a manifestation of multiple rescalings and synthetic SNR enhancements.

Then a hashing projector is applied at step 342 to order the mutations. A diagnostic decision is then rendered at step 344 by examining the order of the mutations and comparing the mutations with a table identifying corresponding diseases.

Thus, the output of block 314 represents all hixels that identify complementary oligonucleotide bindings in the biological sample being analyzed and this represent "mutations". The output of block 335 comprises a set of expressed genes that are associated with a particular pathogenic pathway and thus represent a preliminary "diagnosis". Further analysis of the pathogenic pathway provides a set of possible diseases, if any. This decomposition is motivated by scaling the computation to answer three questions:

Does the current condition imply predisposition to a specific disease?

What is the likelihood of presence of a disease?

What is the set of all possible diseases that may be concluded from the target sample, given a specific genomic encoding implemented by the biochip?

In any case, if the diagnostic decision rendered at step 344 is affirmative, then the diagnosis is output. If the diagnosis is negative then, at step 346, a determination is made as to whether there are any alternative mutations, not within the initial set of mutations selected at step 300, that could be present within the sample. This determination is made by examining a table listing all possible mutations. If there are alternative mutations, then the process is repeated from step 300. If not, then a signal is simply output indicating that no mutations were found in the sample.

Now details of the steps of the new method will be provided. Details regard steps already described in the co-pending application will not be repeated herein.

Mutations Sets

The mutation set of interest generated at step 300 is selected by identifying oligonucleotides representative of the {Z} mutations of interest. Each oligonucleotide is represented by $\psi(i,j)$ which is given by $[\alpha_0 \alpha_1 \ldots \alpha_k]$, where $\alpha=\{A,C,T,G\}$ base associated with each array cell [a,b] where $10 \leq k \leq 25$. The entire set of unique oligonucleotides denoting mutations of interest, $\Delta(l,m)$, is given by $[\delta_0 \delta_1 \ldots \delta_k]$ where $\delta=\{A,C,T,G\}$ length $|\Delta|$=length $|\psi|$, and $0 < \|\Delta - \psi\| \leq k$, and the designed in $\psi(l,m)$ oligonucleotide sequence is a perfect complement to only $\Delta(l,m)$ for all l,m.

As part of step 300, an oligonucleotide table is generated which contains the oligonucleotide sequences associated with each mutation of interest identified by row and column location (i,j). The oligonucleotide table is provided for subsequent use at step 312 to map locations within the dot spectrogram wherein resonance occurs at step 310 to oligonucleotides such that mutations present in a sample being analyzed are easily identified. Also as part of step 300, a mutation table is generated which contains the diseases associated with each mutation of interest. The mutation table is provided for subsequent use at step 314 to map mutations identified at step 312 to specific diseases or other medical conditions such that the diseases can be easily identified.

Basis System for Quantum Expressor Functions

The selection of the basis system and the generation of the QEF's based thereon depends, in part, and the characteristics of the DNA microarray. In the exemplary embodiment, the DNA microarray is an N by M DNA chip array wherein an element of the array is referred to herein as an "oxel": o(i,j).

The pre-hybridization microarray (PEBC) is expressed as:

$$PEBC = \sum_{1}^{N} \sum_{1}^{M} o(i,j),$$

where N and M refer to the linear (row and column) dimensions of the 2-D microarray.

The numeric value associated with each oxel is given by:

$$\hat{O}(i,j) = \alpha_k \cdot 4^{k-1} + \alpha_{k-1} \cdot 4^{k-2} + \ldots + \alpha_1 \cdot 4^1 + \alpha_0 \cdot 4^0$$

where $[\alpha]=[A|C|T|G]$ take the values $[0|1|2|3]$ respectively.

An element of the dot spectrogram is referred to herein as a hixel: h(i,j).

A spin boson basis system is selected for use with this type of array. Other basis system may be appropriate for either the same or other microarray configurations.

Quantum Expressor Functions

The QEF is generated at step 302 based upon the spin Boson basis system by first calculating the Hamiltonian for the system, calculating harmonic amplitudes $|P_m|$ for the Hamiltonian, generating an order function (OF), measuring entrainment entrainment states of the OF of the ground truth and finally modulating the OF of ground truth to yield the QEF.

The QEF's generated at step 302 are converted to a phase-space representation. Also, if the output of the hybridization chip is not in phase space then it is converted as well. The conversion is performed using phase embedding operator, $\Gamma$, described in the co-pending application. Results associated with combinatorial Hopf Algebra are used to contain amplitude dispersion due to loss of hybridization. A special case of quantum random walk, Gelfand-Naimark Segal (GNS) construction is used to disperse group stimulus. Note that coproduct construct of the Hopf algebra plays the role of "sharing out" possible explanations of a fact. The GNS dispersion of QEF is implemented using an approximation:

$$\Phi_{QEF}(\text{amp.vector}) = \hat{U}_i \alpha \hat{U}_i^{-1} \text{ where } \hat{U}_i = e^{-iiH}$$

where H denotes the hamiltonian for the coupling spin boson system.

Generation and Tesselation of the Dot Spectrogram

As noted a dot spectrogram is generated at step 306 for a sample from an N by M DNA chip array wherein an element of the array is an "oxel": o(i,j). A 6-$\sigma$ manufacturing process accuracy in microarray design is assumed. Each array cell amplitude is given by $\Phi(i,j)$ for i:1 to N, and j: 1 to M. Let $\psi(i,j)$ denote the a priori known oligonucleotide given by $[\alpha_0 \alpha_1 \ldots \alpha_k]$, where $\alpha=\{A,C,T,G\}$ base associated with each array cell [a,b] where $10 \leq k \leq 25$. The complimentary strand, derived from unknown sample is denoted by $\vec{\Psi}(i,j)$.

The post-hybridization microarray is treated mathematically using the machinery of equations with aftereffect. Each hixel given by $\Phi(i,j)$ is represented as a cluster of dynamical systems of potentially [CB] correctly bound, [UB] unbound, [PB] partially bound and [IB] incorrectly bound. Thus $[CB]_{\Phi(i,j)} + [UB]_{\Phi(i,j)} + [PB]_{\Phi(i,j)} + [IB]_{\Phi(i,j)} = T_{101\ (i,j)}$ within 0.0001%.

The dot spectrogram $\Phi(i,j)$ is then tessellated to determine idealized ensemble boundaries for forcing downstream resonant action.

Typically, in signal processing applications, high pass or band pass spatial filtering is implemented to enhance SNR in DS matrix. Alternate methods apply a combination of Laplacian or other edge detection filters to enhance signal from arrays cells with a higher hybridization concentration from those of the adjacent cells. These SNR enhancement methods however work only with positive or zero-SNR. Since SNR in general is negative in our case (ultra-low target DNA concentrations), these methods in effect amplify noise or further blur the hixel boundaries.

Tesselation is performed by performing gradient refocusing and resealing as described in the co-pending application. In the alternative, a Dirichlet tessellation operator or a Delaunay triangulation operator are applied to tessellate the dot spectrogram.

Extraction of Local Parametrics and Calculation of Amplitude Wandering

The tessellated image is treated as a metrically transitive random field. All properties associated with a singular (deterministic), homogeneous (i.e., stationary) field are subsumed.

The parametric of most interest is the integrated density of states, given by $$N(\lambda) = \lim_{L\to\infty} \frac{1}{\pi L} E\{\aleph(L)\}$$

$$\text{where } \aleph' = \sqrt{\lambda} - \frac{q}{\sqrt{\lambda}}\sin^2\aleph$$

$$\text{whence } \aleph'|_{\aleph=\pi n} = \sqrt{\lambda} > 0$$

where N is the number of eigenvalues to the system (random field approximation).

This is computed for each tessellation region in the dot spectrogram.

Amplitude wandering is determined using Palm generators as described in the co-pending patent application. The Palm generators exploits the notion of generator functions to capture stochastic variability in hybridization binding efficacy. The exemplary method described herein draws upon results in stochastic integral geometry and geometric probability theory.

"Amplitude wandering estimate" that bounds the hixel amplitude dispersion due to total hybridization losses, is computed using Palm generators over the globally re-scaled dot spectrogram to capture amplitude wanderings and transitions at element, neighboring pair and local ensemble levels. Step 310 provides a measure for each mutation-recognizer centered (MRC-) hixel that is invariant to local degradation. The measure is expressed via the form $$m(Z) = \int_Z f(z)dz$$

where Z denotes the set of mutations of interest. In other words, we determine the function $f(z)$ under the condition that m(Z) should be invariant with respect to all dispersions ξ. Also, up to a constant factor, this measure is the only one which is invariant under a group of motions in a plane. In principle, we derive deterministic analytical transformations on each MRC-hixel, that map error-elliptic dispersion bound defined on $\Psi^2$ (the two dimension Euclidean space—i.e., oxel layout) onto measures defined on $\Psi$. The dispersion bound is given by the form $$\text{Log}_4(\hat{O}_{(i,j)}|^2).$$

Recall that Palm distribution, Π of a translation ($T_n$) invariant, finite intensity point process in $\Psi^n$ is defined to the conditional distribution of the process. It is expressed in terms of a Lebesgue factorization: $E_p N^* = \Lambda L_N \times \Pi$, where Π and Λ completely and uniquely determine the source distribution P of the translation invariant point process. The term $E_p N^*$ denotes the first moment measure of the point process and $L_N$ is a probability measure. In the co-pending application we described how to compute Π and Λ which can uniquely enocde the dispersion and amplitude wandering associated with the MRC-hixel.

In this invention we relax the strong assumption that Palm generators, Π and Λ, capture all sources of stochasticity in dot spectrogram output. Since hybridization losses are affected in unknown and unpredictable ways, we need to modify the generators as probabilistic functions themselves. In other words the generators are converted to manifolds as opposed to a point function.

$(\rho_{m(i,j)}, \sigma_m, \eta_m, \bar{\omega}_m)$ specifies a continuous probability density function for amplitude wandering in the m-th MRC-hixel of interest where the terms denote:

oligonucleotide density per oxel $\rho_{m(i,j)}$, PCR amplification protocol ($\sigma_m$), fluorescence binding efficiency ($\eta_m$) and imaging performance ($\bar{\omega}_m$). Previously we required a preset binding dispersion limit to be apriori provided to compute Λ, given by the second moment to the function at SNR=0.

Nondispersive Π is computed using Π=Θ*P where $$P = \int_{\tau_1}^{\tau_2} \wp(\rho_{m(i,j)}, \sigma_m, \eta_m, \bar{\omega}_m) \partial \tau$$

And $\tau_1$ and $\tau_2$ represent normalized hybridization dispersion limits (typically preset to 0.1 and 0.7 respectively to assume losses between 10%–70% hybridization.

Preconditioned dot spectrogram is represented by Φ(i,j), where function $1/(1+\exp(\wp(\ldots)))$ was used to express the underlying known and stationary point process.

The latter assumption is relaxed in this method and determination of whether the amplitude wandering is within allowable generator function limits is achieved by:

$$\frac{\Pi_0 - |\xi|^2}{\xi_1 \xi_2 \ldots \xi_k} \leq \Pi_0 \leq \frac{\Pi_0 + |\xi|^2}{\xi_1 \xi_2 \ldots \xi_k}$$

where $\Pi_0$ denotes the nondispersive generator.

$\xi_1, \xi_2, \ldots, \xi_k$ provide the Laplace characteristic functional of the Poisson random field associated with each source of hybridization degradation. The contributions are estimated using $$\sqrt{\xi_i} = c_{d} \cdot (det \hat{\alpha}_i)^{\gamma} \lambda_0^{d/2}$$

where c is gain constant and $\hat{\alpha}$ denotes a nonrandom matrix $$\hat{\alpha} = \{\hat{\alpha}_{ij} : 1 \leq i, j \leq d\} \text{ given by}$$

$\hat{\alpha}_{ij} = E\{\alpha_{ik}(\xi)\psi_{kj}(\xi)\}$ and are metrically transitive fields representing the unique solution of the following variational problems:

$$E\{\psi_{li}(\xi)\alpha_{lk}\psi_{ki}(\xi)\} \to \infty \qquad (i)$$

$$rot\,\psi_i = \frac{\partial \psi_{ij}}{\psi_k} - \frac{\partial \psi_{ki}}{\psi_j} = 0 \qquad (ii)$$

$$E\{\psi_{ji}(\xi)\} = \delta_{ji} \qquad (iii)$$

$$E\{\psi_{ji}(\xi)\psi_{ji}(\xi)\} < \infty \qquad (iv)$$

The differential operator for the metrically transitive field for convoling the uncertainty parameters is denoted by $A_0$. Population and solution of the above equation requires estimates for the forward sensitivity matrix of variables impacting hybridization degradation.

Renormalization at step 312, if necessary, is performed on the tessellated image to further match spectral properties of the stimulus pattern The re-normalization of the dot spectrogram is achieved by resealing the dot spectrogram in the interval $[-\pi, +\pi]$. The entire calculation proceeds in the phase space which is why we transformed the system to the metrically transitive random field.

Resonant Interaction to Identify Mutations

As noted, at step 314, the resonant interaction between the QEF and the tessellated, re-normalized dot spectrogram is performed until a pre-selected degree of convergence is achieved. Resonance dynamics relaxation values are calculated at step 316 as follows.

A closed-form convolutionless evolution equation is given by:

$$\varphi_{DST_i}(t) = \Theta(t, \tau) \varphi_{DST_i}(\tau)$$

where $$\frac{\partial \Theta(t, \tau)}{\partial t} = \psi_{DST}(t, \tau) \varphi_{DST_i}(t, \tau)$$

where both depend upon the normalized $DST_i$ (i.e., initial state) at time $\tau$—post-hybridization but pre-conditioned state. And $$\psi_{DST}(t, \tau)$$

is the unitary evoluter $e^{-l(t-\tau)\hat{H}}$ for the hamiltonian specifying the after affect basis system dynamics.

Also, $$\varphi_{DST_i}(t, \tau) \lim_{\varepsilon \to 0} \frac{1}{\varepsilon} \left[ \psi_{DST}(t+\varepsilon, \tau) - 1 \right]$$

In practice a small $\epsilon$, typically $10^{-6}$ is used.

So if theoretical convergence time is $\tau_0$ (outer convergence cycle time) and choosing $t > \tau + \tau_0$, then:

$$\varphi_{DST_i}(t) = \Theta(t, \tau + \tau_0) \varphi_{DST_i}(\tau + \tau_0)$$

and $$\Theta(t, \tau') = \lambda \left[ \int_{t'}^{\tau} \varphi(t') dt' \right]$$

and $\lambda$ is a time-ordering operator.

The dynamics relaxation values are then filtered at step 318 using ensemble boundary and CSR filters (higher order Poisson kernel) as follows:

$$\varphi_{DST_i}(t) * e^{-P(|\Theta|)} \text{ where}$$

$$P_r(|\Theta|) = \frac{1 - r^2}{1 - 2r\cos + r^2} \text{ where } r \geq 0.$$

The bulk property estimators of step 320 are applied to the dynamics relaxation values as follows:

$$\frac{1}{2\pi} \int_{DST_i} P_r(t - |\Theta|) dt$$

where t is the discretization step.

The above expression provides an estimate of when a geometric motion embodied by the convolutionless equation, is no longer a plausible resonance candidate.

This is the closed form for an expression at which the coupling between DST and the microarray is broken and a coupling with a nonlinear information filter (NIF) is established. In essence, the system forgets any initial correlation and tends to a Lindbald condition.

The resonance convergence is determined at step 322 as follows:

$$\text{Log} \frac{|U(t+1) - U_{f\lambda[AVG]}|}{|U(t) - U_{f\lambda[AVG]}|} \geq 1$$

The system oscillates if no convergence is reached. If increasing the timescale x-times (~5) does not meet the condition, then the mutation is deemed to be absent.

It should be noted that, unlike the technique of the co-pending application, in the present invention the absence of resonance over a maximum interation count does not imply absence of resonance. The reason is that both the dot spectrogram and the QEF are dispersed, i.e., the SNR is reduced over an individual hixel, but is in fact increased over an ensemble. So the convergence decisions are made by cascading the inner loop reverberations as opposed to a single reverberation. So two timecycles are used for the convergence analysis:

(a) time cycle over which hyperfine resonances are tracked, detected and used as a decision mechanisms to continue or stop the interation;

(b) time cycle over which the absense of mutation is actually concluded. This is done by implementing a local maxima over output of previous step and then reintegrating. The method essentially accumulates partial resonances and then applies the same resonance equation to the rescaled and renormalized partial stage.

This process can be analytically be represented as:

$$(\tau_1, \tau_2) = \sum_{DST} c_3(\tau_2)$$

$$\left[ \oint c_2(\tau_2) \otimes \left[ \frac{1}{C(\tau_2)} \left| \left[ \sum_{DST} c_1(\tau_2) \otimes \oint_{DST_i} U_{f\lambda[AVG]} d\tau_1 \right] \quad > 0 \right| d\tau_2 \right] \right.$$
$$\left. \qquad\qquad\qquad\qquad\qquad 0 \qquad\qquad\qquad\qquad \text{otherwise} \right]$$

where $c_1$, $c_2$ and $c_3$ are thresholding constants that are used to detect subthreshold resonances. Also, $c_1 >> c_2 >> c_3 >> 1/$[amplitude resolution].

Also $\tau_1$ and $\tau_2$ refer to the inner and outer integration timescales. In an implementation they refer to the iteration conter at which the integration loop is terminated, exceeded or exited. Typically termination counter is set to one thousand steps with timescale of the order of ten nanoseconds for inner step and microsecond for outer step. So effective device convergence time is within one hundred milliseconds for the entire computation.

In this regard, if the Lindbald condition is not achieved and verified the dynamics is considered paralyzed.

The paralysis of dynamics actually implies that coupling between (a) the Quantum Expressor Function,
(b) the tessellated and normalized dot spectrogram, and
(c) the convolutionless carrier is too weak to exhibit a nonlinear resonance. The physical interpretation is that the coupled system exhibits "frustrated dynamics" which enhances and impedes resonance reaction at the same time. So the actual output takes the form of white noise over several hixels which oscillates.

The detection of oscillation occurs when the spectral radius for the convergence criteria oscillates between limits $[\epsilon_1, \epsilon_2]$ and does not tend towards 0. This may be verified by tracking the spectral radius zero crossing with respect to the lower bound $\epsilon_1$. If the zero crossing frequency exceeds a present number (e.g., 10) in this implementation, the dynamics is deemed paralyzed.

If a paralysis of dynamics has occurred, a "mutation death" is evaluated as follows. The check for MRC hixel death relates to the verification of a suprathreshold resonance, where the resonance is defined as the integrand of partial resonances over the entire DST structure, i.e, $$(\tau_1, \tau_2) = \sum_{DST} c_3(\tau_2) \left[ \oint c_2(\tau_2) \otimes \left[ \frac{1}{C(\tau_2)} \left| \left[ \sum_{DST} c_1(\tau_2) \otimes \oint_{DST_i} U_{f\lambda[AVG]} d\tau_1 \right] > 0 \atop 0 \quad \text{otherwise} \right| d\tau_2 \right] > K$$

$\forall \tau_1, \tau_2 \leq$ predefined upper limit. Typically set to 100 for outer iteration and 1000 for inner iterations.

The time scale for realization of the Lindbald condition is changed and the system reiterated.

Hence the final output of step 314 is all hixels that identify complementary oligonucleotide bindings in the biological sample which are represented computationally by the set $\{h_k(i,j)\}$ where $\{h_k(i,j)\}$ is the corresponding oligonucleotide sequence $[\alpha_0 \alpha_1 \ldots \alpha_k]$ for the kth surviving hixel.

Resonant Interaction to Identify Diseases

The mutations identified using block 314 are processed using similar steps within block 325 to identify diseases represented by the mutations. Hence the final output of step 335 is a set of expressed genes that are associated with a particular pathogenic pathway which is represented computationally by the set $\{\psi'_k(i,j)\}$ where $\{\psi'_k(i,j)\}: [\alpha_0 \alpha_1 \ldots \alpha_k]$ for the l-th element of the pathway capturing the k-th disease.

For single disease analysis steps 324–334, i.e., block 335 can be omitted.

Clustering Property Check

Diseases identified using block 325 are processed at step 340 to identify clustering properties as follows. The clustering operation is essentially a pruning operation based on morphological filtering of subthreshold resonances and subsequent recentering (i.e. the inverse of dispersion).

The clustering computation is based on transversal ordering (is based on transversal numbers) of the oligonucleotide sequencing underlying the resonance-centers for all subthreshold resonances. The concept draws from a result in hypergraph theory. Recall that transversal of a hypergraph $H = \{X: E_1, E_2, \ldots, E_m\}$ is defined to be a set $T \subset X$ such that $T \cap E_1 \neq \phi$ for $I=1, 2, \ldots, m$, where $E_1, E_2, \ldots, E_M$ define subgraphs.

In this method, each oligonucleotide, associated with a mutation that survives "hixel-death" during resonant reverberation iterations, is represented by $\psi(i,j): [\alpha_0 \alpha_1 \ldots \alpha_k]$, where $\alpha = \{A, C, T, G\}$ base associated is treated as a subgraph of the total set of unknown mutations that are actually present in the target sample. If the surviving hixel is an ensemble than each ensemble is treated as a subgraph with multiple nodes and several edges. If only an individual hixel survives than it is treated as a single node subgraph. Transversal number of a hypergraph, H, is defined as the minimum number of vertices in a transversal. It is given by:

$$\tau(H) = \min |T|$$

The sub-steps involved in clustering are:
determine Min $\Im = \{A_1, A_2, \ldots, A_k\}$, where $A_1, A_2, \ldots, A_k$ denote the surviving resonance clusters.

Next determine the following families:

$\Im_1 = \{A_1\} \rightarrow Tr\{A_1\} = (\{\alpha\}/\alpha \in A_1)$
$\Im_2 = \Im_1 \cup \{A_1\} \rightarrow Tr\{\Im_2\} = \text{Min}(Tr \Im_1 \vee Tr\{A_2\})$
$\Im_3 = \Im_2 \cup \{A_3\} \rightarrow Tr\{\Im_3\} = \text{Min}(Tr \Im_2 \vee Tr\{A_3\})$
$\Im_4 = \ldots$ If Min A has k members, then the algorithm constructs Tr $A = Tr \theta_k$ in k steps.

Hashing Projector

A bashing projector is then applied at step 342 to the output of the clustering check. The hashing projector produces an enumeration of the leading k oligonucleotides with the highest transveral numbers. So a set of mutations or the corresponding expressed genes are created that have the highest sorted transversal numbers. Typically, all members that are separated by a distance of, at most two, are chosen.

Diagnostic Decision

A diagnostic decision is rendered at step 344 based upon the output of the hashing projector. The diagnostic decision is achieved using a simple table lookup that is indexed by the results of hashing projection computation using the aforementioned tables.

Alternatives

Alternative possible mutations are evaluated at step 346. If alternatives are available, the alternative set of mutations of interest are loaded and the process is repeated beginning at step 300. Hence, if the original set of mutations from which the original set of QIF's were generated during the off-line process of steps 301 and 302, did not include the alternative mutations, then the off-line process is repeated with the new set of mutations to generate new QIF's.

In the event that method yields (and it often does) multiple disease detection hypotheses, all possible hypotheses are provided as plausible candidates.

The technique described with respect to FIGS. 4-A–4-C is particularly powerful in that it provides an enumerative solution which generally covers all possible diagnostic candidates as opposed to only one or two, given the best genomic understanding or mapping between expressed genes and diseases.

Alternative Embodiments

Details regarding an implementation directed to measuring viral loads may be found in co-pending U.S. patent application Ser. No. 09/253,791, now U.S. Pat. No. 6,235,511, also filed contemporaneously herewith, entitled "Exponentially Convergent Therapy Effectiveness Monitoring Using Viral Load Measurements", and also incorporated by reference herein.

The exemplary embodiments have been primarily described with reference to flow charts illustrating pertinent features of the embodiments. Each method step also represents a hardware or software component for performing the corresponding step. These components are also referred to herein as a "means for" performing the step. It should be appreciated that not all components of a complete implementation of a practical system are necessarily illustrated or described in detail. Rather, only those components necessary for a thorough understanding of the invention have been illustrated and described in detail. Actual implementations may contain more components or, depending upon the implementation, may contain fewer components.

The description of the exemplary embodiments is provided to enable any person skilled in the art to make or use the present invention. Various modifications to these embodiments will be readily apparent to those skilled in the art and the generic principles defined herein may be applied to other embodiments without the use of the inventive faculty. Thus, the invention is not intended to be limited to the embodiments shown herein but is to be accorded the widest scope consistent with the principles and novel features disclosed herein.

What is claimed is:

1. A technique for analyzing an output pattern of a biological sample applied to an array to determine the presence of specific constituents within a biological sample applied to the array, wherein the output pattern comprises signals associated with noise, and signals correlating to the biological sample with the signal correlating to the biological sample having intensities both greater and less than the signal associated with noise, the method comprising the step of:
   segmenting the output pattern of the array using tessellation;
   processing the segmented output pattern using interferometry to amplify signals associated with the biological sample, having an intensity lower than the intensity of signals associated with noise, to an intensity greater than the intensity of the signals associated with noise to generate a modified output pattern;
   determining which signals within the modified output pattern are associated with specific constituents within the biological sample; and
   determining specific constituents within the biological sample based on the signals within the modified output pattern associated with specific constituents within the biological sample.

2. A computer code product that determines the presence of specific constituents within an output pattern of a biological sample applied to an array of detectors, wherein the output pattern comprises signals associated with noise, and signals associated with the biological sample which have intensities both greater and less than intensities of signals associated with noise, the computer code product comprising:
   computer code that segments the output pattern using tessellation;
   computer code that utilizes interferometric signal processing to amplify signals within the segmented output pattern associated with the biological sample having an intensity lower than the intensity of the signals associated with noise, to an intensity greater than the intensity of the signals associated with noise to generate a modified output pattern;
   computer code that determines which signals within the modified output pattern correlate the specific constituents within the biological sample; and
   computer code that determines specific constituents within the biological sample based on the signals within the modified output pattern correlating to specific constituents within the biological sample.

3. The computer code product of claim 2 wherein the signal-processing utilizes resonance interferometry to amplify the signals associated with the biological sample.

4. The computer code product of claim 3 wherein the utilized resonance interferometry is either quantum resonance interferometry or stochastic resonance interferometry.

5. The method of claim 1, wherein the segmenting step comprises the step of: tessellating the output pattern to match predetermined morphological characteristics.

6. The method of claim 1, wherein the tessellation is a fuzzy tessellation.

7. The method of claim 1, wherein the segmenting step uses gradient refocusing.

8. The method of claim 1, wherein the segmenting uses at least one of a Dirichlet tessellation operator or a Delaunay triangulation operator.

9. The method of claim 1, wherein the step of processing the output pattern comprises the step of:
   generating a resonance pattern by performing a convergent reverberation to yield a resonance pattern representative of resonances between a predetermined set of Quantum Expressor Functions and the tessellated output pattern until a predetermined degree of convergence is achieved between the resonances found in the resonance pattern and expected resonances.

10. The method of claim 9 wherein the step of iteratively processing the output pattern by performing a convergent reverberation includes the step of performing a convergent reverberant dynamics resonance analysis of the tessellated output pattern using a resonance stimulus pattern to indicators associated with the constituents within the biological sample represented by the tessellated output pattern.

11. The method of claim 10, wherein the step of performing a convergent reverberent dynamics resonance analysis comprises the step of:
   determining resonance dynamics relaxation values based upon the processed output pattern a resonance stimulus.

12. The method of claim 11, wherein the step of performing a convergent reverberent dynamics resonance analysis further comprises the step of: filtering the dynamics relaxation values using ensemble boundary and CSR filters to yield a first set of values.

13. The method of claim 12, wherein the step of performing a convergent reverberent dynamics resonance analysis further comprises the step of: applying bulk property estimators to the dynamics relaxation values to yield a second set of values.

14. The method of claim 13, wherein the step of performing a convergent reverberent dynamics resonance analysis further comprises the steps of:
   evaluating the first and second sets of values to determine a degree of resonance convergence; and
   determining from the degree of resonance convergence whether a paralysis of dynamics has occurred.

15. An apparatus for analyzing an output pattern of a biological sample applied to an array to determine the presence of specific constituents within a biological sample applied to the array, wherein the output pattern comprises signals associated with noise, and signals correlating to the biological sample with the signals correlating to the biological sample having intensities both greater and less than the signals associated with noise, the apparatus comprising:
   means for segmenting the output pattern of the array using tessellation;
   means for processing the segmented output pattern using interferometry to amplify signals associated with the biological sample, having an intensity lower than the intensity of signals associated with noise, to an intensity greater than the intensity of the signals associated with noise to generate a modified output pattern;
   means for determining which signals within the modified output pattern are associated with specific constituents within the biological sample; and
   means for determining specific constituents within the biological sample based on the signals within the modified output pattern associated with specific constituents within the biological sample.

16. The apparatus of claim 15, wherein the means for segmenting comprise means for tessellating the output pattern to match predetermined morphological characteristics.

17. The apparatus of claim 15, wherein the tessellation is a fuzzy tessellation.

18. The apparatus of claim 15, wherein the means for segmenting uses gradient refocusing.

19. The apparatus of claim 15, wherein the means for segmenting uses at least one of a Dirichlet tessellation operator or a Delaunay triangulation operator.

20. The apparatus of claim 15, wherein the means for processing comprises means for generating a resonance pattern by performing a convergent reverberation to yield a resonance pattern representative of resonances between a predetermined set of Quantum Expressor Functions and the tessellated output pattern until a predetermined degree of convergence is achieved between the resonances found in the resonance pattern and expected resonances.

* * * * *